United States Patent [19]
McRae

[11] Patent Number: 5,911,164
[45] Date of Patent: Jun. 8, 1999

[54] COMPACTION AND PAVEMENT DESIGN TESTING MACHINE AND METHOD FOR TESTING FLEXIBLE PAVEMENT MATERIALS

[76] Inventor: John L. McRae, 416 Groome Dr., Vicksburg, Miss. 39180

[21] Appl. No.: 09/021,373

[22] Filed: Feb. 10, 1998

[51] Int. Cl.$^6$ .................................................... G01N 3/00
[52] U.S. Cl. ................................................................ 73/815
[58] Field of Search .............................. 73/803, 794, 795, 73/822, 818, 823, 825, 806, 813, 841, 815

[56] References Cited

U.S. PATENT DOCUMENTS

| | | |
|---|---|---|
| 2,972,249 | 2/1961 | McRae et al. . |
| 3,127,765 | 4/1964 | O'Neil . |
| 3,397,572 | 8/1968 | Stolz et al. . |
| 3,478,572 | 11/1969 | McRae et al. . |
| 3,618,369 | 11/1971 | Hamilton et al. . |
| 4,502,338 | 3/1985 | Smith et al. . |
| 4,569,222 | 2/1986 | Arnold et al. . |
| 4,942,768 | 7/1990 | McRae . |
| 5,036,709 | 8/1991 | McRae . |
| 5,275,056 | 1/1994 | Hamilton et al. . |
| 5,323,655 | 6/1994 | Eagan et al. . |
| 5,456,118 | 10/1995 | Hines et al. . |
| 5,712,431 | 1/1998 | Vilendrer ................................. 73/841 |

*Primary Examiner*—Robert Raevis
*Attorney, Agent, or Firm*—Jacobson, Price, Holman & Stern, PLLC

[57] ABSTRACT

A combination kneader/compactor and plane-strain, simple shear testing apparatus for use in testing paving materials by subjecting them to anticipated design stress over a range of temperatures and various rates of shear. The sample is compacted to the ultimate in-place (equilibrium) density that occurs in the pavement structures. This apparatus and method pre-stresses the sample under the actual stress anticipated for the structure and use the anticipated theoretical vertical stress to fully compact the sample followed by a plane strain simple shear test to measure the dimensionally correct shear strength and moduli which are used to calculate the dimensionally correct design parameters. Pertinent variables are displayed on a computer screen during testing followed by print out of a graph and data sheets with relevant design data. Fundamental engineering (stress-strain) measurements including rational shear strength and static as wall as dynamic moduli are obtained which are suitable for use in design calculations in a rational engineering approach to flexible pavement design in lieu of conventional empirical correlations. The optimum bitumen or water content is precisely determined on the basis of the elasto-plastic property response under simulated traffic, independently of conventional empirical correlations with a percentage of voids and empirical shear indices. Precisely controlled cyclic shear deformation is introduced while the sample is subjected to the anticipated design vertical stress, this being analogous to what happens in the pavement beneath a moving vehicle tire. Thus this laboratory testing machine becomes an accelerated traffic simulator.

25 Claims, 5 Drawing Sheets

COMPACTION AND PAVEMENT DESIGN TESTING MACHINE AND METHOD FOR TESTING FLEXIBLE PAVEMENT MATERIALS

FIELD OF THE INVENTION

The present invention relates to an apparatus and a mix design method for testing samples of granular plastic paving materials such as gravel, stone or soil, which are mixed with water or bitumen and may include additives such as lime or cement and various other chemicals and compounds used to enhance the paving mixture or paving foundation material for flexible pavements.

BACKGROUND OF THE INVENTION

All laboratory compaction and design tests for use in flexible pavement design must duplicate the unit weight (density) of the ultimate in-place pavement materials. Some paving materials compaction and design tests employ a tamping foot (impact or kneading) as the compaction method where the number of tamps of a given magnitude are empirically correlated with the unit weight (density) developed under traffic. These procedures become obsolete when the traffic load changes. Some later developments in paving materials compaction and design tests employ a gyratory kneading action at a given magnitude of vertical stress and angle of kneading in which the number of cycles of kneading are empirically correlated with the unit weight (density) developed under traffic. These test methods also become obsolete when the traffic loads increase above that for the empirically correlated condition.

Other machines used previously for measuring the shear strength and dynamic moduli (compression and rebound) under cyclic loading have simply employed cyclic loading on a confined or unconfined cylinder of the paving material the cylinder receiving no added distortional stress in conjunction with the cyclic vertical stress. This is not analogous to the action occurring in a flexible pavement layer beneath a moving wheel as the pavement layer actually deflects under the load thus introducing a combined action of internal particle movement or so-called kneading action in conjunction with the vertical compression and rebound with the passage of the wheel load.

Examples of conventional arrangements and/or methods are disclosed in the following patents, the teachings of which are hereby incorporated in their entirety by reference:

| PAT. NO. | PATENTEE |
| --- | --- |
| 2,972,249 | McRae et al. |
| 3,127,765 | O'Neil |
| 3,397,572 | Stolz et al. |
| 3,478,572 | McRae et al. |
| 3,618,369 | Hamilton et al. |
| 4,502,338 | Smith et al. |
| 4,569,222 | Arnold et al. |
| 4,942,768 | McRae |
| 5,036,709 | McRae |
| 5,275,056 | Hamilton |
| 5,323,655 | Eagan |
| 5,456,118 | Hines |

SUMMARY OF THE INVENTION

The present invention relates to a compaction and pavement design testing machine and method for flexible pavement materials (subgrade, base and surface layers). Since bituminous mixtures used in the surface courses of flexible pavements are temperature susceptible, this testing machine is provided with a temperature controller. The control regime involves relating the laboratory sample to the actual field condition during placement. This is accomplished by setting the machine mold chuck temperature at an acceptable back-up temperature while placing the sample in the machine at a temperature representing the initial temperature immediately behind the paving machine. Thus, the cooling that occurs during placement is simulated in the laboratory.

Any compaction test for flexible pavement materials is required to duplicate the ultimate in-place unit weight (density). The method proposed herein is to introduce the vertical design stress and attain this fully compacted (equilibrium) condition by this rational engineering approach of pre-stressing under the anticipated design stress and automatically stopping at this fully compacted condition. This automation is achieved by having a computer stop the compaction when the appropriate rate of densification is achieved. This is in lieu of the purely empirical trial and error approach previously described.

In accordance with the invention, the testing machine is a compaction and shear testing machine as well as an accelerated traffic simulator which not only shuts off automatically at the appropriate fully compacted (equilibrium) condition but also identifies the critical condition when excess plasticity begins to occur. This excess plasticity is indicated by a progressive increase in shear strain (gyratory angle) accompanied by a progressive decrease in shear strength (gyratory roller pressure) obviously, the optimum bitumen or water content must be less than that at which this excess plasticity occurs, but not so much less as to cause unfavorable qualities associated with deficient plasticity, resulting in excess porosity accompanied by cracking and raveling. Additionally, the unit weight (density) at the selected optimum must be sufficient to preclude further densification under traffic, which otherwise would result in ruts in response to compaction under traffic.

The testing machine hardware and software are arranged so that, during a compaction and shear test, the vertical pressure, specimen height, gyratory angle (shear strain), and roller pressure (shear strength) are detected, digitized and recorded at the completion of each revolution of a roller carriage. Specimen density is computed at each revolution from the specimen height measurement and the known specimen weight and mold dimensions. Specimen static shear strength and static compression moduli are computed, stored and printed at the conclusion of each test using the roller pressure and the known dimensions of the components of the machine and the force diagram for the machine loading system. The gyratory angle is detected, digitized, and stored continuously during each revolution (or is at least sampled a sufficient number of times during each revolution that the samples represent the continuum of gyratory angles with a predetermined level of accuracy). From this data, the peak to peak gyratory angle for each revolution is computed and recorded.

An analog graph is provided on the computer screen plotting specimen height gyratory angle and roller pressure as a function of roller carriage revolutions. Revolutions are plotted on the horizontal axis to a logarithmic scale for easier operator interpretation of the test results. Specimen height gyratory angle and roller pressure are plotted to an arithmetic scale on the vertical axis. Specimen height density and rate of change of density are also digitally displayed on the computer screen to provide the operator with additional information regarding the test.

The compaction and shear test software is preferably programmed to automatically terminate a test when a selected criteria is reached. For convenience of operation, the software is responsive to a user's selection of a termination condition based on rate of change of density, density, specimen height or number of revolutions. Thus, upon achieving the user-selected condition, the test is automatically terminated. In addition, the operator can manually terminate a test at any time when the analog graph shows that the test specimen has become excessively plastic under the applied test conditions and there is consequently no need to spend additional time on this specimen.

However, according to a preferred embodiment of the present invention, a software program automatically stops the compaction at the point at which the unit weight (density) represents the fully compacted condition (equilibrium) for the selected traffic loading. Since duplicating the ultimate in-place density is absolutely necessary, this represents a major improvement in that it avoids the now obsolete empirical process of sampling the roadway and duplicating the in-place density using a trial and error empirical process.

Upon completion of a compaction and shear test, the operator can print a hard copy of the analog graph displayed on the computer screen. The software is also preferably programmed to automatically compute the significant pavement design parameters related to the test specimen and print out this data.

After a compaction and shear test has been completed, the operator can elect to conduct an additional test in which cyclic vertical loading is combined with a kneading action to simulate the action and reaction in a pavement structure when subjected to the transient loading of a moving vehicle. The testing machine hardware and software are preferably arranged and programmed so that the vertical load on the test specimen is momentarily shifted high for a brief interval (usually one second) and then returned to a lower level for the remainder of each revolution. Specimen height and vertical pressure are measured, digitized and recorded continuously while the cyclic loading test is in progress. An analog plot is continuously provided on the computer screen of the change in specimen height and the corresponding vertical load as the test progresses. This cyclic loading is repeated a sufficient number of times to collect statistically valid measurements. Upon completion of the cyclic loading test, the software preferably computes the dynamic moduli for the test specimen and outputs this information on a data sheet as well as printing a graph of the response versus cycles of loading.

An object of this invention is to provide a materials testing machine that provides a mechanical analogue of a unit of flexible pavement with an associated computer program directing the machine to make measurements and calculations from which significant design parameters can be computed for the flexible pavement specimen under test. These parameters include ultimate unit weight (density), optimum bitumen or water content and plane strain simple shear properties including static as well as dynamic moduli suitable for theoretically sound dimensionally correct, rational design calculations.

Another object of this invention is to provide a software program for conveniently identifying the unit weight (density) at which the rate of densification (density change versus cycles of kneading) has reached a prescribed value representing the fully compacted condition (equilibrium) when employing the anticipated pavement design stress, stopping the compaction at this point and furnishing a printout of the information displayed on the computer screen and a data sheet.

Still another object of this invention is to indicate on the computer screen when the shear strength (roller pressures begins to show a progressive reduction in value with continued densification, indicating a progressively unstable condition with continued densification, thus warning of potential rutting and shoving on the road.

Still yet another object of this invention is to indicate on the computer screen when a test specimen begins to show a progressive increase in the gyratory angle (a measure of shear strain) with continued densification, indicating a progressive loss in shear strength thus warning of potential rutting and shoving on the road.

Yet another object of this invention is to provide means for automatically stopping the compaction process when the rate of densification (density change versus cycles of kneading) has reached a prescribed value.

Yet another object of this invention is to provide means for automatically stopping the compaction process when the height, density or revolutions reach a prescribed value.

Yet another object of this invention is to provide means for automatically computing the significant design parameters using the test measurements and printing these results on appropriate data sheets.

Yet another object of the invention is to provide a granular plastic materials testing apparatus in which the rate of shear can be conveniently and accurately varied in conjunction with variation in temperature so as to reflect the viscosity properties of the material. This feature is particularly valuable when evaluating the affect of additives to enhance the quality of the material used in the various structural layers of flexible pavements.

These and other objects of the invention as well as many of the intended advantages thereof, will become more readily apparent when reference is made to the following description taken in conjunction with the accompanying drawings.

DETAILED DESCRIPTION OF THE PREFERRED EMBODIMENTS

Figure 1:
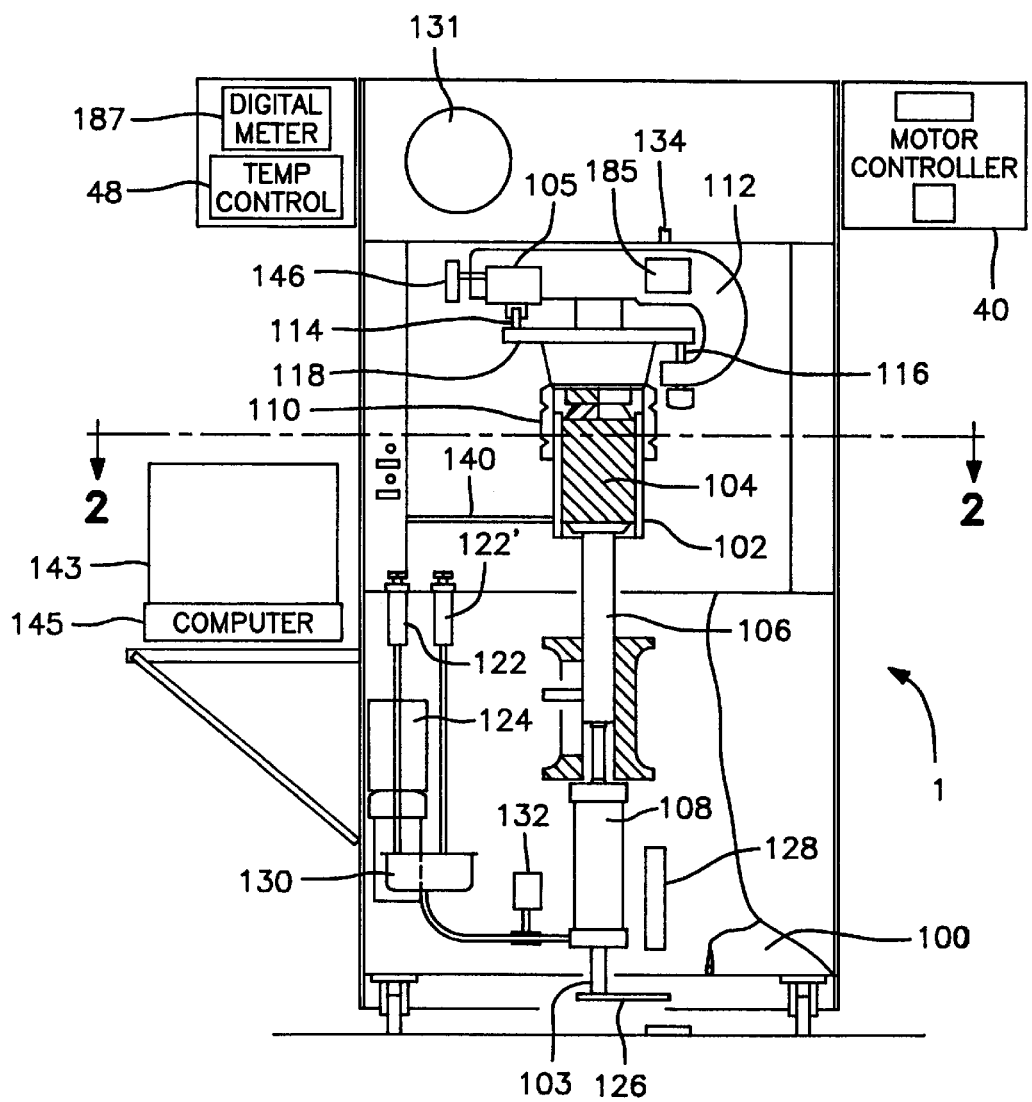
FIG. 1 is a schematic illustration of the testing apparatus of the present invention including principal controls.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 2:
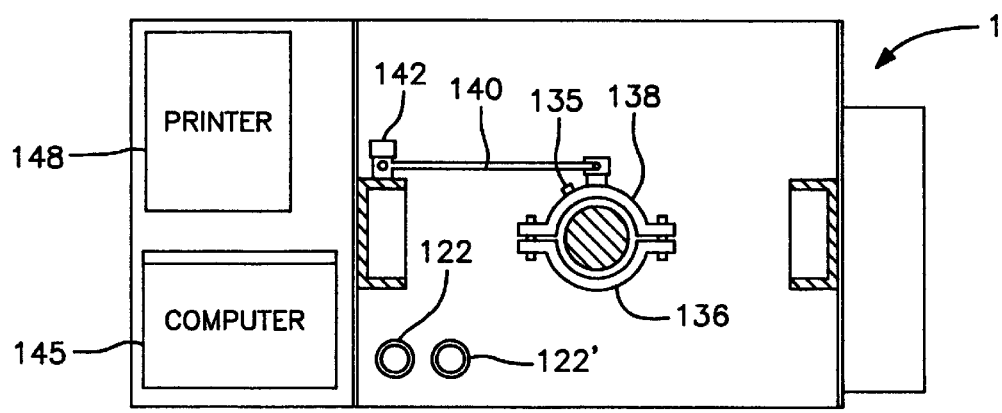
FIG. 2 is a cross-sectional view taken along line 2—2 of FIG. 1.
Figure 3:
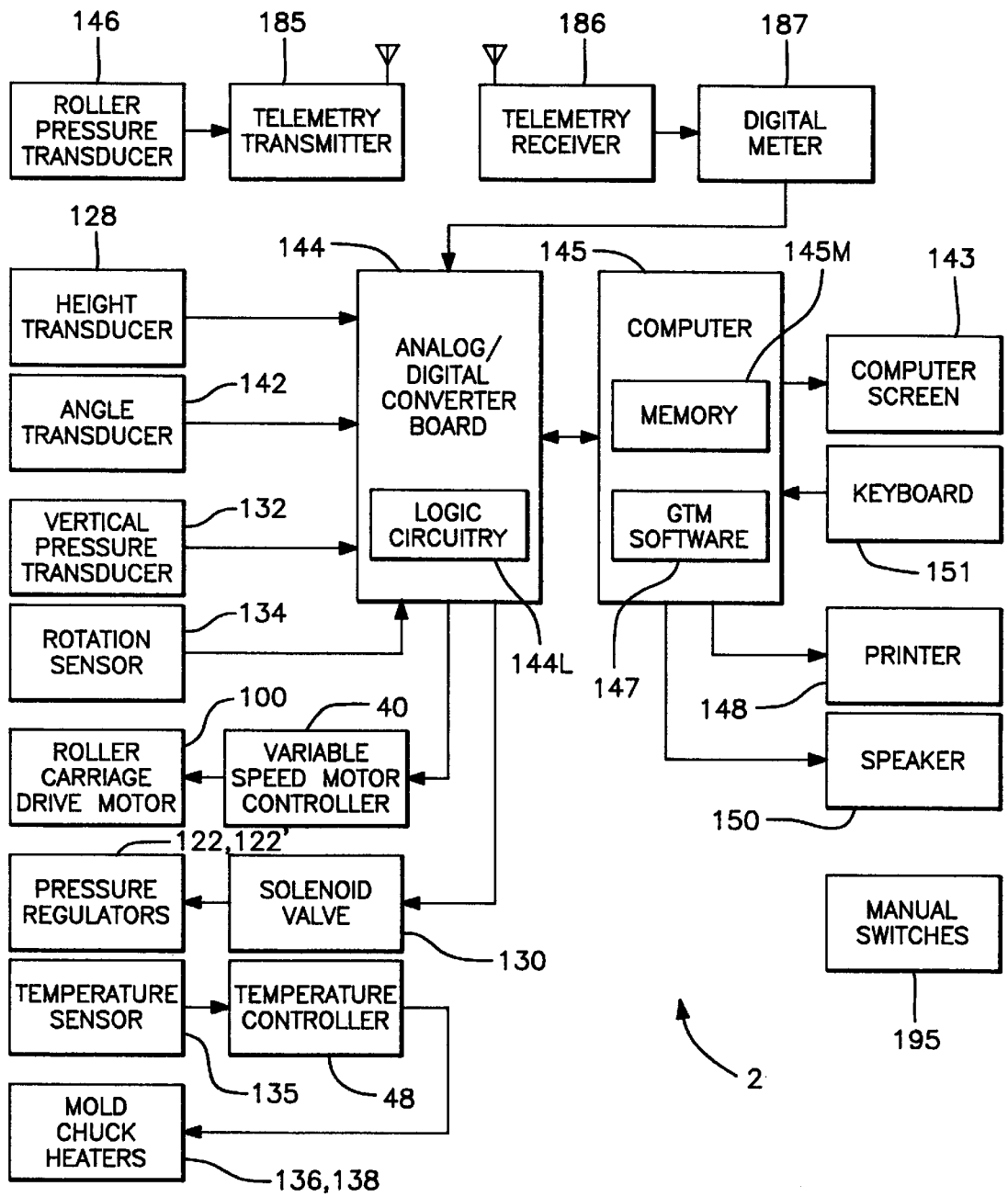
FIG. 3 is a block diagram of a computer-based system that is part of the testing apparatus shown in FIG. 1.

Referring to FIGS. 1, 2 and 3, a preferred embodiment of the present invention includes an testing apparatus 1 and a computer-based control and data acquisition system 2.

The testing apparatus 1 includes pressure control valves 122 and 122' connected to a hydraulic system 124. The hydraulic system 124 is regulated by the control valves 122 and 122' and is arranged so as to drive a double-ended hydraulic cylinder 108. The hydraulic cylinder 108, in turn, is connected to a ram 106 which moves in response to driving of the double-ended cylinder 108 by the hydraulic system 124.

When the testing apparatus is in use, a sample 104 is located at a distal end of the ram 106 so that extension of the ram 106 in response to driving of the hydraulic cylinder 108 causes controlled compression loading of the sample 104. The sample 104 is preferably held within a mold 102 and a mold chuck 110.

Preferably, as shown in FIG. 1, a Bourdon gauge 131 and pressure transducer 132 are connected to the hydraulic system 124 so that the pressure in the hydraulic system 124 is registered by the Bourdon gauge 131. An output of the pressure transducer 132 indicative vertical pressure exerted by the hydraulic system 124 is connected to an analog/digital converter board 144 of the computer-based control and data acquisition system 2. The board 144 includes a power line synchronous integrating analog to digital converter capable of making a measurement on every power line cycle.

The testing apparatus 1 further includes a rotatable roller carriage 112 arranged so as to subject the sample 104 to a gyratory kneading action when the roller carriage 112 is rotated while the sample 104 is under compression forces exerted by the ram 106. A drive motor 100 is operatively connected to the roller carriage 112 to rotate the roller carriage 112 about a vertical axis. The drive motor 100 is preferably powered by an electronic variable-speed motor controller 40 (illustrated schematically in FIG. 3) which allows the user to smoothly start and stop the rotation of the roller carriage 112 and also allows the user to position the roller carriage 112 easily.

Preferably, the electronic variable-speed motor controller 40 is connected to appropriate logic circuitry 144L of the analog/digital converter board 144 and is preferably controlled by such logic circuitry 144L. The logic circuitry 144L therefore is able to selectively stop the drive motor 100 by exercising control over the motor controller 40.

The mold chuck 110 is driven in a gyratory fashion by the action of the roller carriage 112. As illustrated in FIG. 111 the roller carriage 112 of the testing apparatus 1 includes rollers 114 and 116 which are set at different elevations and engage a flange 118 of the mold chuck 110. At least one of the rollers 114 is mounted to the roller carriage 112 via a fluid cell or an air cell 105 such that forces exerted on the roller 114 by the flange 118 are transferred hydraulically or pneumatically to the roller carriage 112 via the fluid contained within the fluid cell or the air contained within the pneumatic cell.

Preferably, this hydraulic or pneumatic coupling is achieved by mounting the upper roller 114 to a reciprocable shaft of the fluid or air cell 105. The reciprocable shaft is arranged so as to define one side of the fluid or air cell 105 in a piston-cylinder-like manner. The hydraulic or pneumatic pressure in the fluid or air cell 105 therefore varies in response to forces exerted longitudinally by the roller 114 against the shaft, which forces are generated by the flange 118 as it bears against the roller 114 when the roller carriage 112 rotates and deforms the sample 104 in the mold 102.

A roller pressure transducer 146 is preferably connected to the fluid or air cell 105 and is responsive to the hydraulic or pneumatic pressure within the fluid or air cell 105. The roller pressure transducer 146 thus provides an output signal indicative of, hydraulic or pneumatic pressure within the fluid or air cell 105. Since this hydraulic or pneumatic pressure is indicative of the shearing resistance of the sample 104, the output signal from the roller pressure transducer 146 is also indicative of shearing resistance.

As illustrated in FIG. 3, the testing apparatus 1 further includes an arrangement for transmitting the information indicative of shearing resistance from the rotating roller carriage 112 to the stationary computer-based control and data-acquisition system 2. Preferably, the roller carriage 112 includes a telemetry transmitter 185, and the output signal from the roller pressure transducer 146 is applied to the telemetry transmitter 185. The telemetry transmitter 185 converts the output signal from the roller pressure transducer 146 into a transmittable signal indicative of the upper roller pressure. In addition, a telemetry receiver 186 is located within the transmitting range of the telemetry transmitter 185. The telemetry receiver 186 receives the transmittable signal and converts it into an analog output signal indicative of upper roller pressure. The telemetry transmitter 185 and telemetry receiver 186 can be any of the well known short range types using radio, infra-red or acoustic links between the rotating roller carriage 112 and the stationary computer-based control and data-acquisition system 2.

Preferably, the analog output signal from the telemetry receiver 186 is applied to a digital meter 187 which converts the analog signal into a digital display of the upper roller pressure using known calibration techniques. Meter 187 also provides an analog voltage proportional to the roller pressure which is fed to the computer analog/digital converter board. This provides the operator with a convenient means of monitoring roller pressure as a test progresses.

The analog output signal from the telemetry receiver 186 is further applied to the analog/digital converter board 144. At the analog/digital converter board 144, the analog output signal from the telemetry receiver 186 is digitized to provide digital information indicative of the upper roller pressure, which digital information is stored in the memory 145M. Alternatively, the telemetry receiver 186 may be arranged so as to produce a digital output which can be applied directly to the computer 145 without having to perform analog to digital conversion.

One possible data acquisition board is available from Cyber Research as an Analog Input Board, Model ACJR16. This board has eight differential analog input channels and twelve digital I/O lines. Four (out of the 8 available) of the analog input channels are used for measuring the signals from the associated transducers. One of the I/O lines (programmed as an input line) is used for the roller carriage rotation sensor. Two of the I/O lines (programmed as output lines) are used to control relays.

The analog input card does not have a digital to analog converter on the board. The digital I/O lines either accept input logic level voltages or output digital logic voltages depending on the way they are programmed.

An important feature of the analog input card used is that an integrating type analog to digital converter is used for the analog input channels. An integrating type analog to digital converter provides a much better signal to noise ratio than that achievable using successive approximation analog to digital converter under the existing electrical noise conditions. In addition the integration period is synchronized with the power line frequency for optimum rejection of power line noise. Also the analog to digital converter must be able to mare a conversion once every power line cycle to achieve sufficient sampling speed.

Control and data-acquisition software 147 is programmed into the computer-based control and data-acquisition system 2 using generally known programming techniques. The software 147 is preferably programed to convert the digital representation of the upper roller pressure into a direct indication of the upper roller pressure on a computer screen 143. The software 147 may be further programmed to convert the digital representation of the upper roller pressure into digital information indicative of shear strength.

Figure 5:
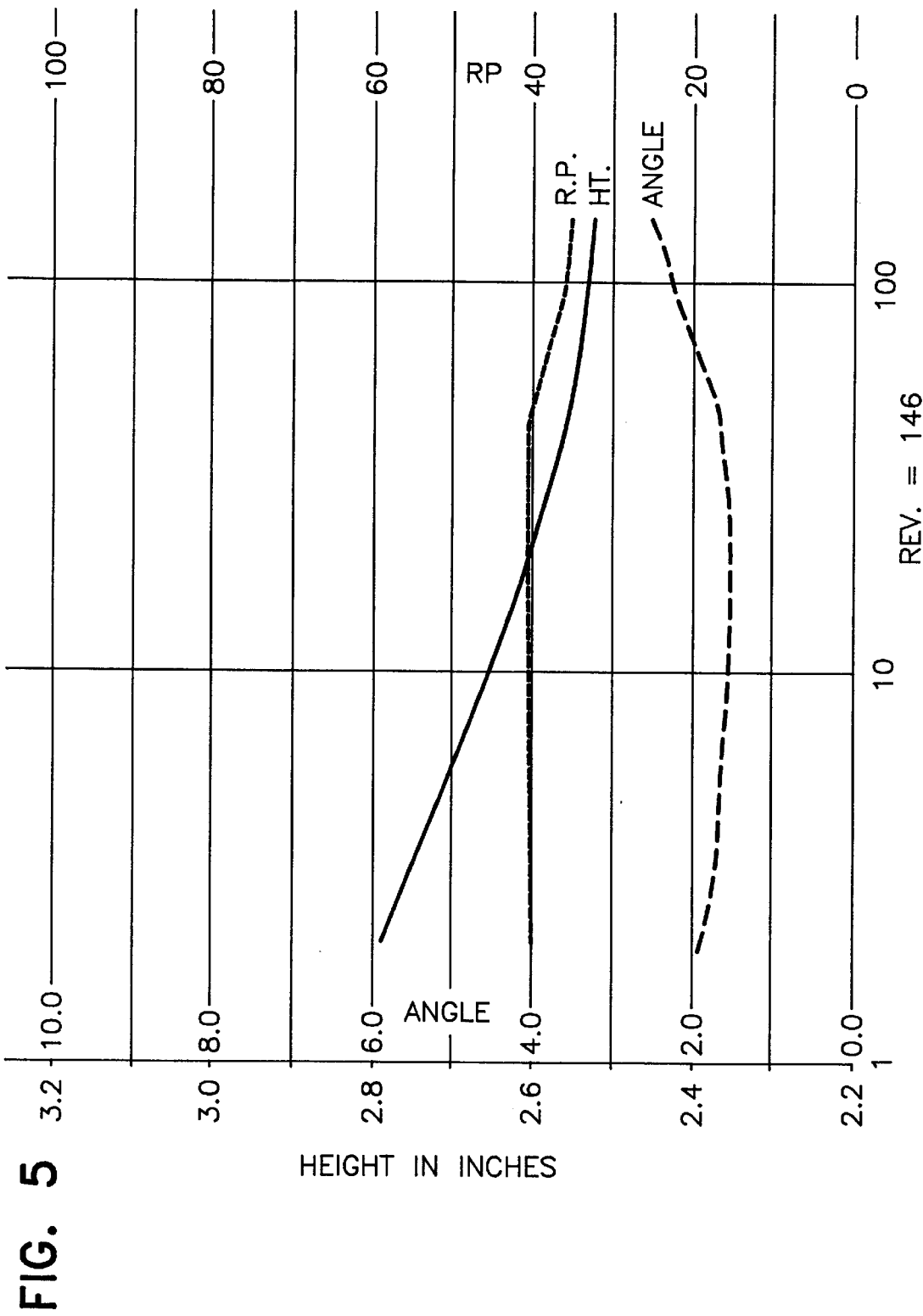
FIG. 5 is a computer print-out of a graph showing shear strain, roller pressure and sample height versus cycles of gyratory kneading.

According to a preferred embodiment, the software 147 causes the computer screen 143 to generate a graphical display of the upper roller pressure, an example of which is illustrated in FIG. 5. The graphical display is preferably provided in real-time during a test, thus providing the operator with additional insight into the stability of the sample 104 under test even as the test progresses.

The software 147 is further programmed, according to the preferred embodiment, to generate via a printer 148 a hard-copy of the graphical information displayed on the computer screen 143 of a lap top computer, as well as a summary data sheet including the roller pressure converted to the shear strength.

The bottom roller 116 is preferably mounted to the roller carriage in an adjustable manner which permits raising and lowering of the bottom roller 116 with respect to the roller carriage 112. Such raising or lowering of the bottom roller 116 permits adjustment of an initial machine setting for the gyratory angle of the mold chuck 110. The term "initial machine setting for the gyratory angle" hereinafter refers to the initial gyratory angle which is established by such adjustment of the bottom roller 116.

The pressure sensing element of cell 105 may be either air or oil, thus defining an oil cell or an air cell, the two types of cells being interchangable.

For tests using the air cell 105, the pressure within the air cell 105 is preferably set at a value corresponding to a safety factor of one with regard to maximum induced shear. Since the air contained within the air cell 105' is compressible, the gyratory angle varies in response to the shearing resistance developed in the sample 104 during testing.

In tests using the oil cell 105, by contrast, the oil remains substantially incompressible. The gyratory angle (machine setting) therefore does not change. For this reason, the air cell 105' is considered to represent a better mechanical analogue of the pavement, having an enhanced sensitivity to the shearing resistance within the material as it experiences the shearing phenomena of dilation and collapse of the aggregate particles.

The testing apparatus further includes a rotation sensor 134 responsive to each revolution of the roller carriage 112. The sensor may be any of several known types such as optical or magnetic sensors. As illustrated in FIG. 3, the output from the rotation sensor 134 is applied to the analog/digital converter board 144, where the output signal is converted into digital information indicative of roller carriage rotation for use by the computer 145.

The hydraulic cylinder 108 preferably includes an indicator bar 126 mounted to an end 103 of the hydraulic cylinder 108. The indicator bar 126, in turn, is connected to a height transducer 128. The height transducer 128 is responsive to linear displacement of the indicator bar 126 and may comprise any one of several known linear displacement transducers, such as a linear variable differential transformer or a potentiometer.

When the hydraulic cylinder 108 causes the ram 106 to move, the end 103 of the hydraulic cylinder causes a corresponding linear displacement of the indicator bar 126. This linear displacement of the indicator bar 126 represents a change in the height of the sample 104, as modified by the linear displacement of the ram 106. The output signal produced by the height transducer 128 is therefore indicative of not only the linear displacement of the ram 106 but also the height of the sample 104.

As illustrated in FIG. 2, this output signal from the height transducer 128 is applied to the analog/digital converter board 144. The analog output signal from height transducer 128 is then digitized and stored in a computer memory 145M. Alternatively the height transducer 128 may be arranged so as to produce a digital output which can be applied directly to the computer 145 without having to perform analog/digital conversion.

The control and data-acquisition software 147 is preferably programmed to convert the digital representation of the height transducer's output signal into a direct indication of the sample's height and unit weight (density). Preferably, the software 147 is further programmed to display on the computer screen 143 the height of the sample 104.

According to a preferred embodiment the software 147 causes the computer screen 143 to generate a graphical display of the sample's height, an example of which is illustrated in FIG. 5. The sample's density is preferably calculated based on the height and is stored in the computer memory 145M by the software 147. In addition, the software 147 is preferably programmed to calculate, based on the density, a rate-of-change of the density driving each revolution of the roller carriage 112.

Preferably, the computer 145 is programmed to respond to a rate-of-change indicative of equilibrium by terminating rotation of the roller carriage 112. An exemplary rate-of-change indicative of equilibrium would be a rate-of-change of less than one pound per cubic foot per 100 revolutions.

The testing apparatus 1 further comprises front and rear mold chuck heaters 136 and 138, a temperature controller 48 for controlling the mold chuck heaters 136 and 138, and a temperature sensor 135 having an output signal indicative of temperature connected to the temperature controller 48. The mold chuck heaters 136 and 138 provide a means whereby the temperature of the mold chuck 110 can be maintained at a temperature selected by the pavement engineer when testing bituminous mixtures. The temperature sensor 135 is attached to the mold chuck 110 and is arranged so as to provide its output signal as feedback to the temperature controller 48. The temperature controller 48 selectively adjusts the electrical energy sent to the mold chuck heaters 136 and 138 to maintain the temperature of the mold chuck 110 at the set point programed into the temperature controller 48.

With reference to FIG. 2, an extension of the mold chuck 110 projects out from a rear face of the mold chuck 110. A linkage 140 has a first end connected to the extension of the mold chuck 110 and an opposite end connected to an angle transducer 142. The angle transducer 142 is arranged with respect to the linkage 140 so that the angle transducer 142 is influenced only by the vertical component of oscillations of the first end of linkage 140. The vertical component of oscillations, in turn, is proportional to the angle of gyration (gyratory angle) of mold chuck 110 during rotation of the roller carriage 112. Therefore, the angle transducer 142 produces an output signal indicative of the gyratory angle.

The angle transducer 142 may be any of several types, for example, potentiometric, capacitive or inductive, and it preferably produces an output signal that is directly and linearly proportional to the gyratory angle. The output signal from the angle transducer 142 is connected to the analog/digital converter board 144 of the computer-based control and data acquisition system 2. The output signal from the transducer 142 is preferably analog and is digitized at a high sampling rate compared to the gyratory motion. Alternatively the transducer 142 may be arranged to provide a digital output signal at a high sampling rate compared to the gyratory motion, in which case there is no need to digitize the signal.

The software 147 is programmed to detect, for each revolution of the roller carriage (as detected by the rotation sensor 134), the highest and lowest values obtained by the output signal from the angle transducer 142. The difference between the highest and lowest values is indicative of the peak-to-peak value of the gyratory angle for each revolution of the roller carriage The software 147 is preferably programmed to convert the peak-to-peak value detected via the angle transducer 142 into a direct indication of gyratory angle in degrees and this value is stored by the software 147 into the memory 145M. The software 147 is preferably programmed to also present the indication of gyratory angle in a graphical display on the computer screen 143 as illustrated in FIG. 5.

Referring again to FIG. 1, it will be appreciated that although the gyratory angle about the line connecting the rollers 114 and 116 is fixed by the relative elevations of these rollers, the mold chuck 110 is free to tilt about that line by an angle greater than that which is set by the rollers 114 and 116. Thus, the magnitude of the full cycle of the gyratory angle is not the initial (machine setting) angle set by the inclination of the line connecting the rollers 114 and 116 but rather is a function of the internal shearing resistance and the elasto-plastic properties of the sample 104. This unique feature is made possible by mounting the mold chuck 110 in such a way that it essentially floats on the mold 102 and the sample 104 during the test. This unique sensitivity is an important feature of the present invention. This feature allows the aggregate in the sample 104 to experience the shearing phenomenon of dilation and collapse with minimal breakage of aggregate.

The graphical display in FIG. 5, which represents a print-out of what is displayed on the computer screen 143, shows the three principal design indices for flexible pavement materials that are supplied by the testing apparatus and method of the present invention. These include the gyratory angle which is a measure of shear strain, the height of the sample 104 from which the unit weight (density) is calculated and stored in memory 145M for subsequent printout via the printer 148, and the upper roller pressure from which, by calibration conversion, the dimensionally correct rational shear strength is calculated and stored in the memory 145M for print-out via the printer 148.

The graphical display illustrated in FIG. 5 includes the gyratory angle (shear strain) versus cycles of kneading (revolutions of the roller carriage 112). Referring to FIGS. 1, 2 and 5, it will be seen that shear strain measured via the angle transducer 142 is a function of the motion of carriage 112. As the sample 104 is kneaded, its plasticity is reflected by the gyratory angle. As the sample compacts, the gyratory angle initially becomes smaller due to an increase in strength with increase in unit weight (density). For a stable mix, the gyratory angle will reach a minimum and become essentially constant. If the sample 104 becomes unstable due to over-filled voids, the angle will start to increase with further densification. A continued reduction in the gyratory angle indicates deterioration of the aggregate due to breakage in response to kneading. The beginning of a progressive increase in the gyratory angle, as illustrated by the recording in FIG. 5 represents a critical measurement in the design and control of the paving mixture. As stated earlier, an increase in the gyratory angle (shear strain) indicates that the sample 104 would be unstable under the load simulated by the testing procedure and would be an unacceptable pavement mixture.

As indicated above, the software 147 is preferably programmed to include in the computer screen and print-out graph of FIG. 5 an indication of the upper roller pressure versus cycles of kneading (revolutions of roller carriage 12). As the sample 104 is subjected to cycles of kneading, its shearing resistance as reflected by the upper roller pressure will vary. A stable condition for the sample 104 is reflected by an increase in this reading as the density increases and then a leveling off at an essentially constant value. If, however, the sample 104 becomes unstable, the upper roller pressure will decrease significantly reflecting a reduction in the shear strength. This reduction in shear strength accompanies the increase in shear strain (gyratory angle) as described above. These two engineering parameters of shear strength and shear strain are direct rationally measured properties that the engineer relies upon in the design of flexible pavements.

As stated above, in flexible pavement design testing it is absolutely essential that the laboratory sample duplicate the ultimate in place unit weight (density). As stated earlier, a paramount feature of the inventive apparatus and method is the introduction of the concept of achieving this fully compacted (equilibrium) condition by compacting and testing under the anticipated vertical stress that occurs beneath the tire of a vehicle. The density of the sample is a direct function of the height of the sample since it is based upon the weight of the sample and the volume of the mold. For this reason the change in height versus cycles of kneading, as shown in the computer printout of FIG. 5, forms the basis for defining and controlling the degree of compaction required to simulate the in-place field condition. As indicated above, this is specified in terms of the slope of the curve of unit weight (density) versus cycles of kneading.

The computer 145 is preferably programmed to detect this slope and to automatically stop the test when a specified rate of densification is attained. Thus, the problem of empirically relating the laboratory compactions to the field by trial and error is alleviated.

The measured values of vertical pressure, upper roller pressure, height of sample and gyratory angle (shear strain) described above are correlated with the number of revolutions of roller carriage 12. These parameters are displayed on the computer screen during testing and the parameters of this graphical display are stored and also printed out at the conclusion of the test. These variables are indices that accurately reflect the performance of the sample but they must be converted to rational engineering parameters of stress and strain in terms of the physical dimensions of the machine before they are applicable for use in the design analysis.

Figure 4:
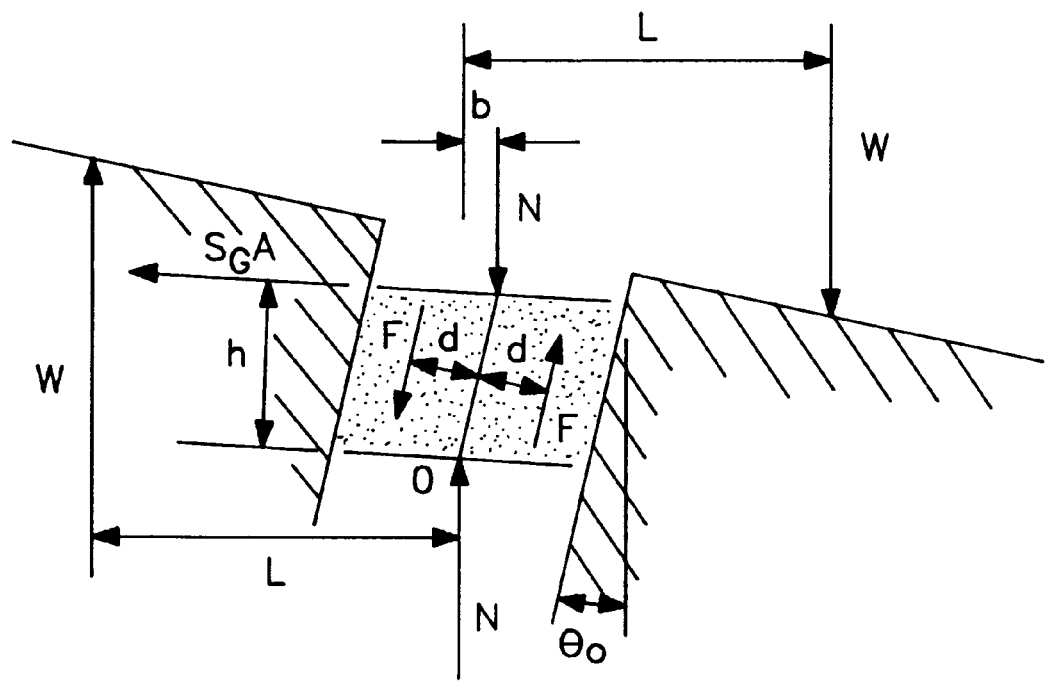
FIG. 4 is a schematic illustration of a model used to derive formulas for calculation of gyrating shear and gyrating moduli, including correction for wall friction.

FIG. 4 shows a force diagram for the testing apparatus 1 in which the interrelationships of the converted parameters are used to calculate rational, dimensionally correct values of shear strength, shear strain and moduli. The dynamic moduli are not included in these derivations. However, it is understood that the dynamic moduli simply involve calculations based upon measured values of compression and rebound when the vertical load is cycled during kneading which, in turn, simulates actual traffic.

The following are the derivations of the formulas for calculation of gyratory shear and gyratory moduli including correction for wall friction. Referring to FIG. 4, Gyratory Shear is defined as follows:

$$2 \cdot W \cdot L = S_G \cdot A \cdot h + 2 \cdot F \cdot d - N \cdot b$$

$$S_G = \frac{2(P \cdot L - F \cdot d) + N \cdot b}{A \cdot h}$$

where

W=Load on upper roller supper roller pressure multiplied by the effective area of the piston in the fluid cell 105);

L=Distance between the center of the upper roller's path of reciprocation and a centrally located vertical axis of the sample 104;

$S_G$=Gyratory shear;

A=Surface area at the end of the sample h=Height of the sample 104;

F=Frictional force from mold wall friction;

d=Arm of wall friction couple;

N=Vertical load on the sample 104; and b=Arm of vertical force couple (h tan $\Theta_0$)

The Gyratory Shear Modulus is expressed by the formula:

$$G_G = \frac{S_G}{\tan \theta_0}$$

where $S_G$=Gyratory shear; and $\theta_0$=Gyratory machine angle of shear

The Gyratory Compression Modulus is expressed by the formula:

$$E_G = 2G_G(1+\mu)$$

where $G_G$=Shear Modulus; and $\mu$=Poisson's ratio

An exemplary wall friction accessory that measures wall friction F between a sample and a mold is described in U.S. Pat. No. 3,478,572, incorporated herein in its entirety by reference.

The following is an abbreviated approximation for $S_G$ neglecting wall friction (F) and moment (N·b):

$$2 \cdot W \cdot L = S_G \cdot \int A dh = S_G \cdot A \int dh = S_G \cdot A \cdot h$$

$$S_G = \frac{2 \cdot P \cdot L}{A \cdot h}$$

The testing apparatus 1 is preferably arranged to also achieve cyclic vertical loading. In particular, such cyclic vertical loading is achieved using the pressure regulators 122 and 122' which, in turn, are used to set the high and low values for the cyclic loading. A solenoid valve 130 is connected to the hydraulic system 124 and pressure regulators 122 and 122' in such a manner that the state of the solenoid valve 130 determines which of the regulators 122 and 122' is active. Preferably, the software 147 is programmed so that the computer 145 controls the solenoid valve 130 via the analog/digital converter board 144. In particular, the solenoid valve 130 is controlled by the computer 145 so as to periodically activate each regulator 122 or 122', thereby causing the ram 106 to apply predetermined compressive forces to the sample 104.

As indicated above, the pressure transducer 132 preferably provides an electrical signal which is linearly proportional to the pressure in the hydraulic system 124, which pressure is displayed by the Bourdon gauge 131. The signal proportional to hydraulic pressure may be digitized and converted to an indication of the vertical pressure on the sample 104 using a calibration process.

This cyclic mode of loading is analogous to that which occurs in flexible pavement beneath a wheel of a moving vehicle, which loading includes the kneading-type action caused by flexing of the structure, combined with cyclic vertical loading caused by passage of the vehicle over the pavement surface. This kneading action results because the pavement deflects (like a loaded beam) as the wheel passes over the surface.

Figure 6:
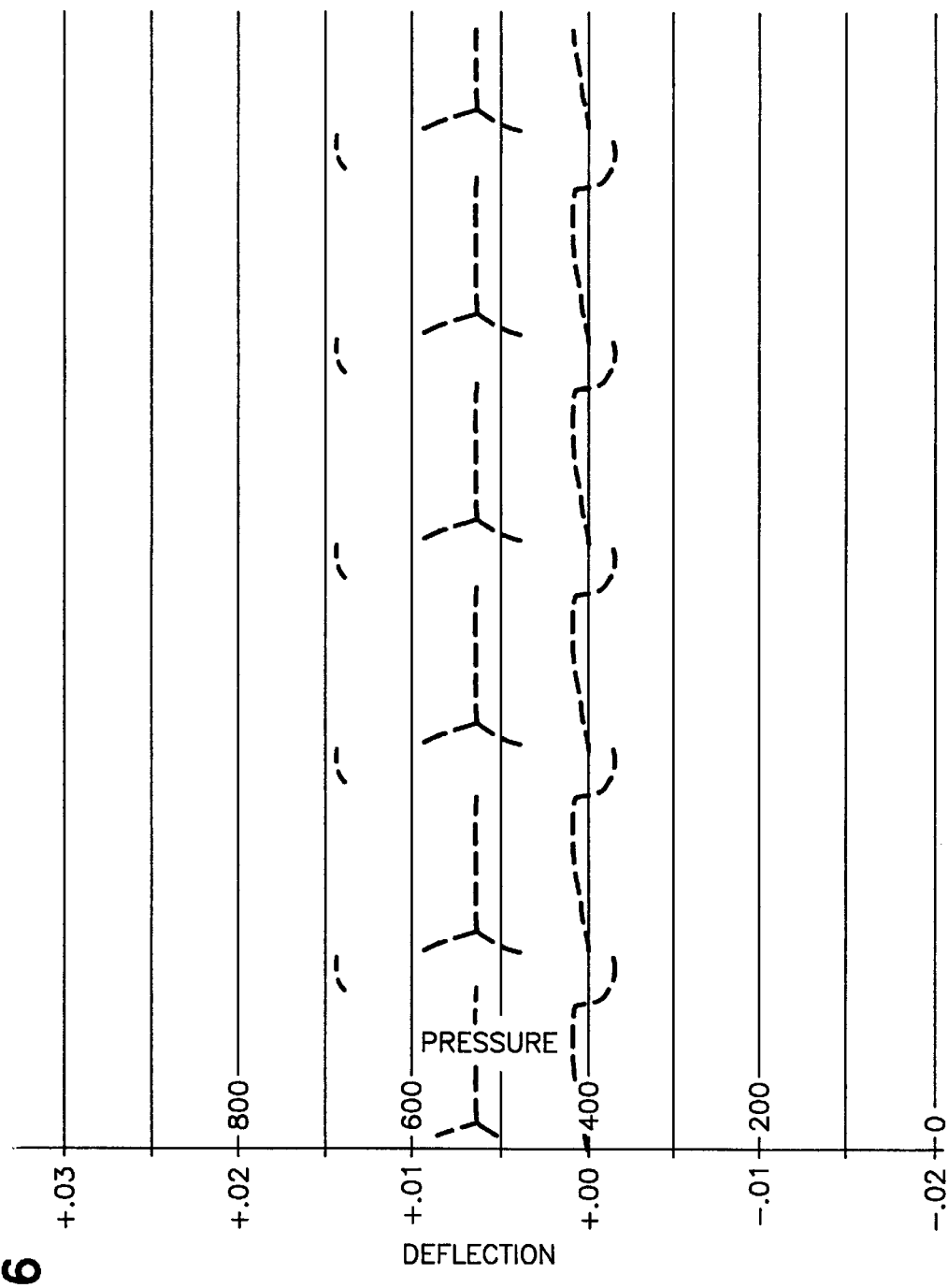
FIG. 6 is a computer print-out of an analog graph of cyclic loading.

FIG. 6 is a print-out of a preferred graphic display on the computer screen 143 which is generated by the software 147 of the computer 145 during the cyclic loading test.

As indicated above, a preferred computer-based control and data-acquisition system 2 is illustrated in FIG. 3. Electrical signals from the various sensors and transducers (e.g., height transducer 128, angle transducer 142, pressure transducer 132 and rotation sensor 134) are provided as inputs to the analog/digital converter board 144. The analog/digital converter board 144, then converts these analog electrical signals into corresponding digital signals, and applies these digital signals to the computer 145 for appropriate processing.

Although the preferred embodiment utilizes sensors and transducers having analog output signals, it is understood that if any of the various transducers is capable of providing a digital output signal, such a digital output signal may be applied directly to the computer 145 without conversion by the analog/digital converter 144. Likewise, if the computer 145 includes an input port which is responsive to analog signals, the analog/digital converter board 144 may be by-passed.

In addition to processing the information represented by the output signals from the sensors and transducers, the computer 145 under the control of the software 147 provides output signals capable of controlling the solenoid valve 130 and the variable speed motor controller 40.

Preferably, the computer-based control and data-acquisition system further comprises at least one speaker 150 connected to the computer 145. The software 147 in the computer 145 is preferably programmed to respond to completion of testing, by activating the speaker 150 in a manner indicative of test completion. The speaker 150 could be activated by the computer 145 to, for example, emit a beep.

Likewise, the software 147 may be programmed so that the computer 145 generates a visual indication of test completion via the computer screen 143. Backup storage of the test information onto floppy disks is preferably made readily available by appropriately programming the software 147 and incorporating a floppy disk drive in the computer 145.

Preferably, the software 147 is programmed to generate, during the tests prompts on the computer screen 143 which alert or warm the operator that preselected or critical conditions have been reached. The system operator can control operation of the testing apparatus via a keyboard 151 connected to the computer, and/or via manually operated switches 195 which are located at strategic points on the testing apparatus.

In operation, the sample 104 to be tested is placed in the mold 102 and the testing apparatus 1 is activated. In response to activation of the testing apparatus 1, the ram 106 is pushed upward into the mold 102 to compress the sample 104 and the roller carriage 112 rotates to subject the sample 104 to kneading. Signals from the various transducers are supplied to the computer-based control and data acquisition system 2 to monitor the compaction and the number of gyratory cycles. Data derived from the various transducers is then used to make the aforementioned calculations, and preferably, the data and the results from the calculations are registered by the computer 145. Registering of the data and results of the calculations may comprise any combination of storage in the memory 145M, displaying on the screen 143 and/or printing of a hard-copy.

Throughout the test, the computer screen 143 provides a continuous graphical display for the operator to monitor. This graphical display shows when the peak-to-peak gyratory angle reaches a minimum and whether or not it increases. The gyratory angle, as indicated above, is a direct measure of shear strain in the material being tested. Both the minimum and maximum values of gyratory angle are used in calculating the predicted performance of the material being tested. The operator may choose values for any of the variable factors by using an appropriate keyboard input and decides whether an oil cell or an air call 105 is to be used.

Preferably, the computer 145 is further programmed to provide informational messages on the computer screen 143 regarding how to use the testing apparatus 1. In this regard, the computer 145 may prompt the user via the computer screen 143 to enter necessary information using a computer keyboard 151 and to carry out other steps which are required in conducting a test using the apparatus 1. The informational messages may also include messages indicative of steps to be taken in order to setup and determine calibration factors for all transducers so that signal voltages from each transducer can be converted to appropriate engineering units during a test.

Preferably, the computer 145 contains different programs depending on which type of material is being tested and is programmed to prompt the user to enter, via the keyboard 151, information indicative of which material is being tested (e.g., bituminous mixtures or soil and aggregate material). In response to this information, the computer 145 executes an appropriate program.

An example of a printout of the stored compaction and shear tests results for a bituminous mixture when using an air cell is given below. The air cell pressure of 24 psi set for these tests is based on the design compaction stress of 120 psi. The air cell pressure to use in a given test is that which represents theoretical maximum shear for the anticipated tire contact pressure. The air cell pressure set for the test example given below is equal to the tire contact pressure of 120 psi divided by 3.14.

Air cell installed 2.0 degrees initial angle 24 psig in air cell for test
Test material G-11A base course with 5.5% oil, reused
Mold chuck is being operated at 26° C.
Performance test
Mold Size=4
Compaction Stress=120 PSI (827 kPa)
TauMax=38.0 PSI (262 kPa)
Total Specimen Weight=1229.0 grams
Percent Bitumen=5.5%
Dry Aggregate Weight=1200.7 grams
Weight of Bitumen=28.3 grams

COMPACTION TEST RESULTS

Compaction terminated at equilibrium at 146 Revolutions
Height at Compaction Termination=2.521 inches (6.4031 cm)
Unit Weight Total Mix=149.6 lbs/cu. ft (2396.3 kg/cu m)
Intermediate Gyrograph=1.52 degrees
Gyrograph at Compaction Termination=2.52 degrees
Machine Angle at end of test=1.33 degrees.
Gyratory Stability Index ThetaFinal/ThetaInterm. GSI)= 1.65

STATIC SHEAR RESULTS WITHOUT WALL FRICTION CORRECTION

| | |
|---|---|
| Average Dynamic Roller Pressure at End of Compaction | = 34.8 psig |
| | = (240 kPa) |
| Average Static Roller Pressure at End of Compaction | = 34.7 psig |
| | = (239 kPa) |

Static Shear Strength (Sg)=55 PSI (380 kPa)
Gyratory Shear Factor=Sg/TauMax, (GSF)=1.45
Static Shear Modulus (Gg)=2371 PSI (16344 kPa)
Static Compression Modulus (Eg)=7112 PSI (49033 kPa)
Poisson's Ratio used in computation=0.50
Static Compression Strain (Predicted)=0.0169 in/in (or cm/cm)
Critical Pressure (p')=24.1 psig (166 kPa)

A printout of the stored data and calculations for the dynamic compression modulus and the dynamic rebound (resilient) modulus would include, for example:
In the following tabulation the data represents measurements from three different pulses for each parameter

| | | | | | |
|---|---|---|---|---|---|
| Higher level (pulse) pressure | = | 688 | 688 | 688 | psig |
| | = | 4744 | 4742 | 4746 | kPa |
| Higher level (pulse) Stress | = | 121 | 121 | 122 | PSI |
| | = | 838 | 837 | 838 | kPa |
| Pulse Width = 0.5 seconds | | | | | |
| Lower level (pre-pulse) Stress | = | 529 | 529 | 528 | psig |
| | = | 3647 | 3649 | 3642 | kPa |
| Lower level (pre-pulse) Stress | = | 99 | 99 | 99 | PSI |
| | = | 682 | 682 | 681 | kPa |
| Cyclic Change in Stress | = | 22.6 | 22.5 | 22.8 | PSI |
| | = | 156 | 155 | 157 | kPa |

| | | | | | |
|---|---|---|---|---|---|
| Low to high pressure transition total deformation | | | | | |
| | = | .00186 | .00191 | .00204 | inches |
| | = | .00472 | .00486 | .00518 | cm |
| Machine Correction (deformation without specimen) | | | | | |
| | = | .00113 | .00113 | .00114 | inches |
| | = | .00287 | .00286 | .00290 | cm |
| Specimen Height | = 2.519 inches | | | | |
| | = 6.398 cm | | | | |

| | | | | | |
|---|---|---|---|---|---|
| Low to high pressure transition specimen deformation | | | | | |
| | = | .0007 | .0008 | .0009 | inches |
| | = | .00184 | .00200 | .00229 | cm |
| Low to high pressure transition specimen strain | | | | | |
| | = | .00029 | .00031 | .00036 | In/Inch or cm/cm |
| Kneading Dynamic Compression Modulus | | | | | |
| | = | 78537 | 72211 | 63819 | Ave. = 71522 PSI |
| | = | 541494 | 497877 | 440015 | Ave. = 493129 kPa |

-continued

| High to low pressure transition specimen deformation | | | | |
|---|---|---|---|---|
| = | .0008 | .0007 | .0008 | inches |
| = | .00199 | .00180 | .00200 | cm |
| High to low pressure transition specimen strain | | | | |
| = | .00031 | .00028 | .00031 | In/Inch or cm/cm |
| Kneading Dynamic Rebound Modulus | | | | |
| = | 73081 | 80797 | 72486 | Ave. = 75455 PSI |
| = | 503877 | 557079 | 499772 | Ave. = 520243 kPa |

According to a preferred embodiment of the present invention, the computer 145 is programmed to respond to predetermined user inputs, which predetermined user inputs cause the computer 145 to vary the speed of carriage rotation (rate of shear) and the temperature of the sample 104 so as to accurately reflect viscosity and strength variations in the mixture as a result of the use of additives which are intended to enhance the quality of the pavement mixture being tested.

Having described the invention, many possible modifications thereto will become apparent to those skilled in the art to which it pertains without deviation from the spirit of the invention as defined by the scope of the appended claims.

I claim:

1. A material testing apparatus for testing samples of flexible pavement materials, said materials testing apparatus comprising:
   a mold for holding the sample of paving material;
   a compactor extending into said mold and capable of compacting said sample when said sample is located within said mold;
   a floating mechanism for compacting said sample of paving material by a gyratory kneading of the paving material while at the same time measuring a shearing resistance of the paving material to dilation and collapse with minimal breakage of aggregate, said mechanism including a mold chuck floating on the sample so that gyration of the mold chuck reflects development of instability by direct response in terms of shearing resistance, as defined by progressive reduction in said force applied by said sample against said mechanism during compaction, and in terms of excess plasticity, as defined by progressive increase in gyratory angle during compaction and kneading to indicate a condition of instability during the compaction for identification of maximum permissible bitumen content of the sample under design stress conditions;
   a heater mechanism and temperature controller for heating the sample to simulate thermal conditions experienced during in-field placement of the material by initially elevating the temperature of the sample to an initial temperature measured immediately behind a paving machine and said temperature controller permitting cooling of the sample during compaction to a temperature measured during field use;
   a controller and data acquisition system including:
      a first sensor responsive to a force applied by said sample against said mechanism during compaction;
      a second sensor responsive to a gyratory angle achieved by said mechanism in response to compaction and kneading of said sample;
      a third sensor responsive to a height of said sample as compacted by said compactor;
      a computer responsive to said first, second and third sensors, said computer being programmed to sample output signals from said first, second, and third sensors during compaction and kneading of said sample and being further programmed to register data indicative of the force applied by said sample against the mechanism, indicative of said gyratory angle, and also indicative of said height,
      said computer being further programmed to automatically terminate testing of a sample in response to detecting satisfaction of at least one termination criterion, said computer being further programmed to accept data indicative of said at least one termination criterion from a user, said at least one criterion being selected from a group of criteria including
         equilibrium of the sample as determined based on a rate-of-change in sample density;
         a predetermined density of the sample;
         a predetermined height of the sample; and
         occurrence of a predetermined number of revolutions of said mechanism, and
      said computer being further programmed to respond to predetermined user inputs by varying a rate of shear of the sample and by varying the temperature of the sample so as to accurately reflect viscosity and strength variations in the sample as a result of the use of additives which are intended to enhance the quality of the sample being tested.

2. The apparatus of claim 1, and further comprising a fourth sensor responsive to revolutions of said mechanism, said computer being responsive to said fourth sensor and being programmed to correlate said data with the revolutions of said machine such that said data is registered as a function of revolutions.

3. The apparatus of claim 2, wherein said computer is further programmed to register said data at least once during each revolution of said mechanism.

4. The apparatus of claim 2, wherein said computer is programmed to register data indicative of said gyratory angle a predetermined number of times during each revolution of the mechanism, said predetermined number being sufficient to capture peak-to-peak values of said gyratory angle.

5. The apparatus of claim 1, and further comprising a display mechanism connected to and responsive to said computer, said computer being programmed to display a graph of said test data.

6. The apparatus of claim 5, wherein said display mechanism is a display screen.

7. The apparatus of claim 5, wherein said display mechanism is a printer.

8. The apparatus of claim 5, and further comprising a fourth sensor responsive to revolutions of said mechanism, said computer being responsive to said fourth sensor and being programmed to correlate said test data with the revolutions of said mechanism such that said test data is registered as a function of revolutions;
   said computer being further programmed such that said graph shows the gyratory angle, the height of the sample, and the force applied by said sample against the mechanism, all of which are plotted with respect to the number of revolutions of the kneading mechanism.

9. The apparatus of claim 1, wherein said computer is further programmed to calculate and register a peak-to-peak gyratory angle based on the output from said second sensor, said computer being further programmed to display said peak-to-peak gyratory angle.

10. The apparatus of claim 1, wherein said computer is further programmed to calculate the density of the sample based on the height of the sample, as detected via the third sensor.

11. The apparatus of claim 1, wherein said computer is further programmed to, based on said test data, calculate and register shear strength, shear factor, stability index, static compression modulus, and dynamic compression and rebound moduli associated with said sample.

12. The apparatus of claim 1, wherein said computer is further programmed to provide informational messages regarding how to calibrate and use the apparatus.

13. The apparatus of claim 1, wherein said computer is further programmed to control actuation of said compactor and said mechanism.

14. The apparatus of claim 13, wherein said computer is further programmed to actuate said compactor and said mechanism in a cyclic manner so that said sample is subject to cyclic loading, said computer being further programmed to calculate moduli of said sample.

15. The apparatus of claim 14, and further comprising a compactor pressure sensor for detecting pressure applied in said compactor to achieve compaction of said sample, said computer being programmed to sample output signals from said third sensor and said compactor pressure sensor numerous times during each cycle of said cyclic loading.

16. The apparatus of claim 15, wherein said computer is further programmed to register a graph indicating changes in said pressure applied in said compactor and also indicting changes in height of said sample, said graph being recorded numerous times during each cycle of said cyclic loading.

17. The apparatus of claim 16, wherein said computer is programmed to calculate dynamic compression and rebound moduli based on said test data and additional test data obtained during said cyclic loading.

18. The apparatus of claim 1, wherein said mechanism includes said mold chuck which floats on the sample in such a way that gyration of the mold chuck reflects any deterioration that may occur in an aggregate phase of the sample, as indicated by a progressive reduction in gyratory angle.

19. A control and data acquisition system for a testing apparatus capable of testing a sample of paving material, wherein the testing apparatus includes a mold for holding the sample of paving material; a compactor operatively connected to the mold and capable of compacting the sample when the sample is located within the mold; a heater and temperature controller for heating the sample to simulate thermal conditions experienced during in-field placement of the sample; and a kneading mechanism for kneading the sample in a gyratory manner during compaction by the compactor, said control and data acquisition system comprising:

first sensor responsive to a force applied by the sample against the kneading mechanism during compaction;

a second sensor responsive to a gyratory angle achieved by the kneading mechanism in response to compaction and kneading of the sample;

a third sensor responsive to a height of the sample as modified by the compactor; and a computer responsive to said first, second and third sensors, said computer being programmed to sample output signals from said first, second, and third sensors during compaction and kneading of said sample and being further programmed to register test data indicative of the force applied by said sample against the kneading mechanism, indicative of said gyratory angle and also indicative of said height;

said computer being further programmed to automatically terminate testing of a sample in response to detecting satisfaction of at least one termination criterion, said computer being further programmed to accept data indicative of said at least one termination criterion from a user, said at least one criterion being selected from a group of criteria including:

equilibrium of the sample as determined based on a rate-of-change in sample density;

a predetermined density of the sample;

a predetermined height of the sample; and occurrence of a predetermined number of revolutions of said kneading mechanism, and said computer being further programmed to respond to predetermined user inputs by varying a rate of shear of the sample and by varying the temperature of the sample so as to accurately reflect viscosity and strength variations in the sample as a result of the use of additives which are intended to enhance the quality of the sample being tested.

20. The control and data acquisition system of claim 19, and further comprising a display mechanism connected to and responsive to said computer, said computer being programmed to display a graph of said test data via said display mechanism; and a fourth sensor responsive to revolutions of said kneading mechanism, said computer being responsive to said fourth sensor and being programmed to correlate said test data with the revolutions of said kneading machine such that said test data is registered as a function of revolutions;

said computer being further programmed such that said graph shows the gyratory angle, the height of the sample, and the force applied by said sample against the kneading mechanism, all of which are plotted with respect to the number of revolutions of the kneading mechanism.

21. The control and data acquisition system of claim 19, wherein said computer is further programmed to, based on said test data, calculate and register shear strength, shear factor, stability index, static compression modulus, and dynamic compression and rebound moduli associated with said sample.

22. The control and data acquisition system of claim 19, wherein said computer is further programmed to provide informational messages regarding how to calibrate and use the apparatus.

23. The control and data acquisition system of claim 19, wherein said computer is further programmed to actuate said compactor and said kneading mechanism in a cyclic manner so that said sample is subject to cyclic loading, said computer being further programmed to calculate moduli of said samples.

24. A material testing apparatus for testing samples of flexible pavement materials, said materials testing apparatus comprising:

a mold for holding the sample of paving material;

a compactor extending into said mold and capable of compacting said sample when said sample is located within said mold;

a floating mechanism for compacting said sample of paving material by a gyratory kneading of the paving material while at the same time measuring a shearing resistance of the paving material;

a heater mechanism and temperature controller for heating the sample to simulate thermal conditions experienced during in-field placement of the material;

a controller and data acquisition system including:

a first sensor responsive to a force applied by said sample against said mechanism during compaction;

a second sensor responsive to a gyratory angle achieved by said mechanism in response to compaction and kneading of said sample;

a third sensor responsive to a height of said sample as compacted by said compactor;

a computer responsive to said first, second and third sensors, said computer being programmed to sample output signals from said first, second, and third sensors during compaction and kneading of said sample and being further programmed to register data indicative of the force applied by said sample against the mechanism, indicative of said gyratory angle, and also indicative of said height, said computer being further programmed to respond to predetermined user inputs by varying a rate of shear of the sample and by varying the temperature of the sample so as to accurately reflect viscosity and strength variations in the sample as a result of the use of additives which are intended to enhance the quality of the sample being tested.

25. A material testing apparatus for testing samples of flexible pavement materials, said materials testing apparatus comprising:

a mold for holding the sample of paving material;

a compactor extending into said mold and capable of compacting said sample when said sample is located within said mold;

floating mechanism for compacting said sample of paving material by a gyratory kneading of the paving material while at the same time measuring a shearing resistance of the paving material to dilation and collapse with minimal breakage of aggregate, said mechanism including a mold chuck floating on the sample so that gyration of the mold chuck reflects development of instability by direct response in terms of shearing resistance, as defined by progressive reduction in said force applied by said sample against said mechanism during compaction, and in terms of excess plasticity, as defined by progressive increase in gyratory angle during compaction and kneading to indicate a condition of instability during the compaction for identification of maximum permissible bitumen content of the sample under design stress conditions; and a heater mechanism and temperature controller for heating the sample to simulate thermal conditions experienced during in-field placement of the material;

a controller and data acquisition system including:

a first sensor responsive to a force applied by said sample against said mechanism during compaction;

a second sensor responsive to a gyratory angle achieved by said mechanism in response to compaction and kneading of said sample;

a third sensor responsive to a height of said sample as compacted by said compactor;

a computer responsive to said first, second and third sensors, said computer being programmed to sample output signals from said first, second, and third sensors during compaction and kneading of said sample and being further programmed to register data indicative of the force applied by said sample against the mechanism, indicative of said gyratory angle, and also indicative of said height, said computer being further programmed to respond to predetermined user inputs by varying a rate of shear of the sample and by varying the temperature of the sample so as to accurately reflect viscosity and strength variations in the sample as a result of the use of additives which are intended to enhance the quality of the sample being tested.

* * * * *